(12) United States Patent
Anderson et al.

(10) Patent No.: US 7,176,244 B1
(45) Date of Patent: Feb. 13, 2007

(54) USE OF 2-NITROPROPANOL, 2-NITROETHANE, AND 2-NITROETHANOL FOR CONTROL OF MICROBIAL PATHOGENS

(75) Inventors: Robin C. Anderson, College Station, TX (US); David J. Nisbet, Bryan, TX (US); Yong Soo Jung, Jonesboro, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 470 days.

(21) Appl. No.: 10/319,986

(22) Filed: Dec. 16, 2002

(51) Int. Cl.
*A01N 33/18* (2006.01)
(52) U.S. Cl. .................. 514/727; 514/740
(58) Field of Classification Search ............ 514/644, 514/645, 579, 727, 740
See application file for complete search history.

(56) References Cited

U.S. PATENT DOCUMENTS 2,888,421 A * 5/1959 Adams et al. ............ 523/122

FOREIGN PATENT DOCUMENTS

WO    WO 9603042    * 2/1996

OTHER PUBLICATIONS

Kido et al., Archives of Microbiology (1975), 106(3), 165-9.*
Anderson, R. C.; Rasmussen, M. A.; Allison, M. J. Appl. Environ. Microbiol. 1996, 62, 3885-3886.*
Anderson, R. C.; Rasmussen, M. A.; Dispirto, A. A.; Allison, M. J. Can. J. Microbiol. 1997, 43, 617-624.*
Anderson, R. C.; Rasmussen, M. A.; Jensen, N. S.; Allison, M. J. Int. J. Sys. Evol. Microbiol. 2000, 50, 633-638.*
Srinivasan, A.; Dick, J. D.; Perl, T. M. Clinical Microbiology Reviews 2002, 15, 430-438.*
http://www.ericbrc.org/portal/eric/enteropathogen?id=entero.*
R.C. Anderson et al., Inhibitory Effect of Nitrocompounds on Ruminal Methane Production in Vitro, Preceedings, Western Section, American Society of Animal Science, vol. 52, 2001.
W. Majak et al., Metabolism of Aliphatic Nitro Compounds in Bovine Rumen Fluid, Canadian Journal of Animal Science, 60:319-325 (Jun. 1980).
W. Majak, Further Enhancement of 3-Nitropropanol Detoxification by Ruminal Bacteria in Cattle, Canadian Journal of Animal Science, 72:863-870 (Dec. 1992).

(Continued)

*Primary Examiner*—Sreeni Padmanabhan
*Assistant Examiner*—Kevin Capps
(74) *Attorney, Agent, or Firm*—John D. Fado; Randall E. Deck; Lesley Shaw

(57) ABSTRACT

The invention provides a method and compositions for controlling food borne enteric bacterial pathogens in animals. Populations of enteropathogenic bacteria may be substantially reduced or eliminated by treatment of animals with an effective amount of 2-nitropropanol, 2-nitroethane or 2-nitroethanol. The compounds may be administered orally, providing a reduction in the populations of the enteropathogenic bacteria in the alimentary tract of the animal, or they may be applied externally onto the animal to reduce the populations of any such bacteria which may be present as contaminants on the surface of the animal. The method and compositions are particularly useful for the control of *Salmonella* species, enteropathogenic *Escherichia coli*, *Campylobacter* species, and *Listeria monocytogenes*.

23 Claims, 8 Drawing Sheets

OTHER PUBLICATIONS

W. Majak et al., Enhanced Degradation of 3-Nitropropanol by Ruminal Microorganisms, J. Anim. Sci. 62:1072-1080, 1986.

R.C. Anderson, Nitropropionate Reduces CH4 Production by Ruminal Microbes, 23rd Biennial Conference on Rumen Function, Chicago, Illinois, Nov. 14-16, 1995, vol. 23.

Robin C. Anderson et al., Use of a Novel Nitrotoxin-Metabolizing Bacterium to Reduce Ruminal Methane Production, Bioresource Technology 64:89-95, 1998.

Humberto G. Monardes et al., Preservation and Storage Mechanisms for Raw Milk Samples for Use in Milk-Recording Schemes, Journal of Food Protection, vol. 59, No. 2, pp. 151-154.

* cited by examiner

USE OF 2-NITROPROPANOL, 2-NITROETHANE, AND 2-NITROETHANOL FOR CONTROL OF MICROBIAL PATHOGENS

BACKGROUND OF THE INVENTION

1. Field of the Invention

This invention relates to a process for the control of enteric bacterial pathogens in animals using 2-nitropropanol, 2-nitroethane, or 2-nitroethanol.

2. Description of the Prior Art

Despite the efforts of researchers and public health agencies, the incidence of human infections from enteropathogenic bacteria such as *Salmonella, E. coli* O157:H7, and *Campylobacter* has increased over the past 20 years. For example, the number of actual reported cases of human *Salmonella* infection exceeds 40,000 per year. However, the Communicable Disease Center estimates that the true incidence of human *Salmonella* infections in the U.S. each year may be as high as 2 to 4 million. The USDA Economic Research Service has recently reported that the annual cost of the food borne illnesses caused by six common bacterial pathogens, *Campylobacter* spp., *Clostridium perfringens, Escherichia coli* O157:H7, *Listeria monocytogenes, Salmonella* spp., and *Staphylococcus aureus*, ranges from 2.9 billion to 6.7 billion dollars (Food Institute Report, USDA, AER, December, 1996). In addition to the impact of enteric pathogens on human health, many of these bacteria also cause significant infections in animals. For example, *Salmonella* infections in swine alone cost the United States swine industry more than 100 million dollars annually (Schwartz, 1990, "Salmonellosis in Midwestern Swine", In: Proceedings of the United States Animal Health Assoc., pp. 443–449).

Animal food products remain a significant source of human infection by these pathogens. Contamination of meat and poultry with many bacterial food-borne pathogens, including the particularly onerous pathogens *Campylobacter* spp., *Escherichia coli* O157:H7, and *Salmonella* spp., often occurs as a result of exposure of the animal carcass to ingesta and/or fecal material during or after slaughter. Any of the above-mentioned pathogens can then be transmitted to humans by consumption of meat and poultry contaminated in this manner.

Preharvest control of enteropathogenic bacteria is a high priority to the food industry. However, few products have been developed to facilitate such efforts. Currently, preharvest pathogen control within the poultry industry may be accomplished through use of competitive exclusion cultures or probiotics. In fact, at this time, only one such product, developed by Nisbet et al. of the USDA Agricultural Research Service (U.S. Pat. No. 5,478,557) and sold under the trademark PREEPMT (Milk Specialties Biosciences, Dundee, Ill.), is available commercially in the United States. Moreover, the administration of competitive exclusion cultures is preferably targeted to very young animals. Immune lymphokines (ILK) have also been developed for protecting poultry from colonization with enteric pathogens as described by Ziprin et al. (1989, Poult. Sci., 68:1637–1642), McGruder et al. (1993, Poult. Sci., 72:2264–2271), Ziprin et al. (1996, Avian Dis., 40:186–192), and Tellez et al. (1993, Avian Dis., 37:1062–1070), and more recently by Kogut et al. (U.S. Pat. Nos. 5,891,443 and 5,691,200). Most recently, Anderson et al. (U.S. Pat. No. 6,475,527) disclosed that chlorates substantially reduce populations of enteropathogenic bacteria in the alimentary tract when administered orally, or alternatively, reduce the populations of these enteropathogens present as contaminants on the surface of the animals following external application of chlorates.

However, despite these and other advances, the need persists for technologies for controlling enteric pathogens in animals, and particularly for the treatment of animals immediately prior to slaughter.

SUMMARY OF THE INVENTION

We have now discovered a method and compositions for controlling food borne enteric bacterial pathogens in animals. Populations of enteropathogenic bacteria may be substantially reduced by treatment of animals with an effective amount of a nitro compound selected from 2-nitropropanol, 2-nitroethane, or 2-nitroethanol, as well as salts thereof or mixtures thereof. The compounds may be administered orally, providing a reduction in the populations of the enteropathogenic bacteria in the alimentary tract of the animal, or they may be applied externally onto the animal to reduce the populations of any such bacteria which may be present as contaminants on the surface of the animal. The method and compositions are particularly useful for the control of *Salmonella* species, enteropathogenic *Escherichia coli*, and *Campylobacter* species.

In accordance with this discovery, it is an object of this invention to provide a method for controlling food borne enteropathogenic bacteria in animals.

Another object of this invention is to provide a method for controlling enteropathogenic bacteria in the gastrointestinal tract of animals.

Yet another object of this invention is to provide a method for significantly reducing the populations of enteropathogenic bacteria in meat producing animals prior to slaughter.

Other objects and advantages of this invention will become readily apparent from the ensuing description.

DETAILED DESCRIPTION OF THE INVENTION

Figure 1:
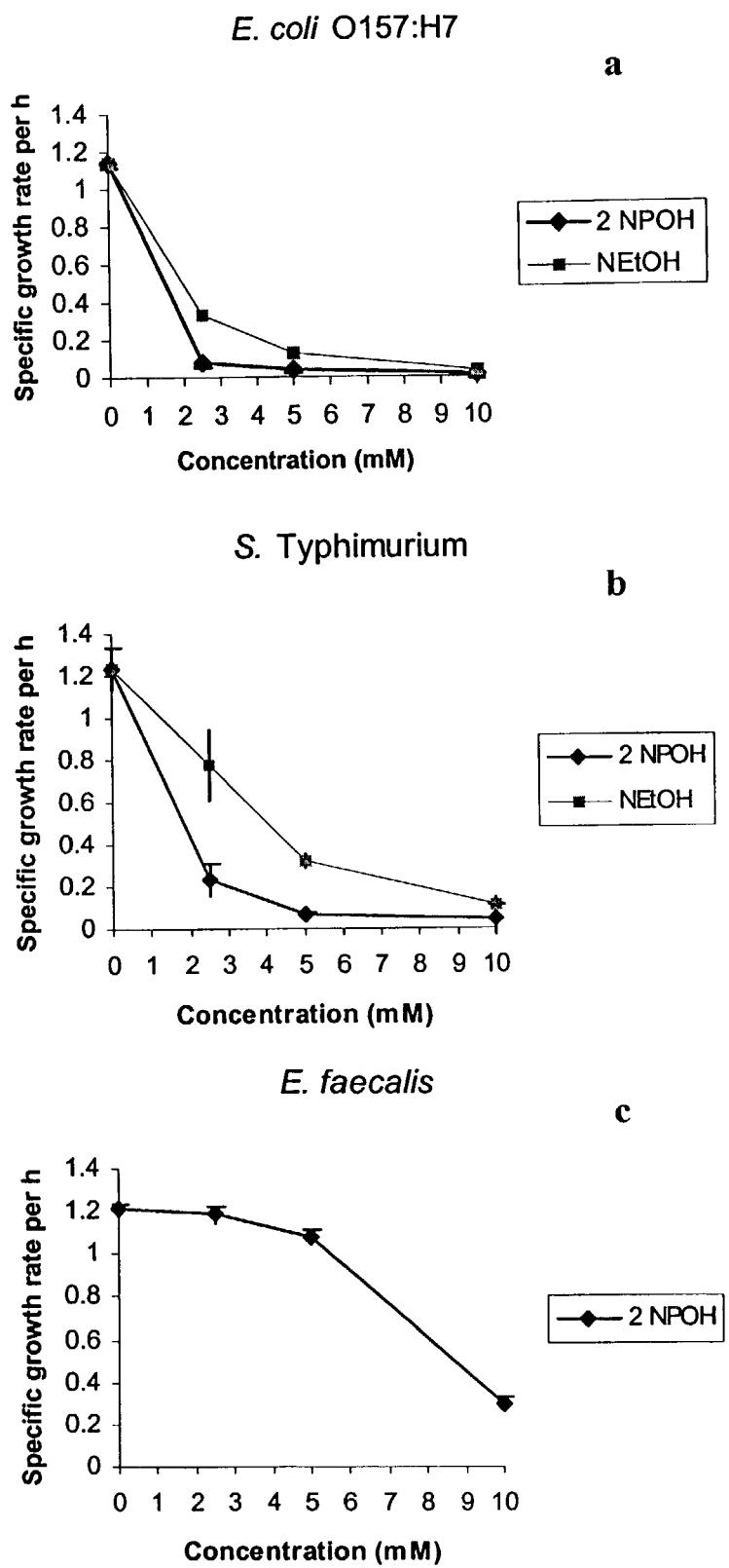
FIG. 1 shows the specific growth rate ($h^{-1}$) (n=3) of (a) *E. coli* O157:H7, (b) *S. typhimurium*, and (c) *E. faecalis* in TSB at different concentrations of 2-nitropropanol (2NPOH) and 2-nitroethanol (NEtOH). Error bars indicate standard deviation.

Any one or a combination of 2-nitropropanol, 2-nitroethane, 2-nitroethanol, or their salts, are effective for controlling or killing several different enteropathogenic bacteria. For the purpose of this invention, the term nitro compounds is defined herein to collectively refer to the above-mentioned group of 2-nitropropanol, 2-nitroethane, 2-nitroethanol, and their salts. Without being limited thereto, preferred salts include alkaline earth metals, such as sodium and potassium salts. A variety of enteropathogenic bacteria may be controlled with the nitro compounds, including but not limited to, *Salmonella* species such as *S. typhimurium* and *S. cholerasuis*, enteric *Escherichia coli* pathogens such as enterohemorrhagic *E. coli* (EHEC, e.g., *E. coli* O157:H7), enterotoxigenic *E. coli* (ETEC), enteropathogenic *E. coli* (EPEC), and enteroaggregative *E. coli* (EAEC), *Campylobacter* species such as *C. jejuni*, and *Listeria monocytogenes*. It is also envisioned that the nitro compounds may also be effective for control of other enteropathogenic bacteria such as *Clostridium perfringens*.

Depending upon the route of treatment, the nitro compounds are effective for reducing the populations of the enteropathogenic bacteria within the gastrointestinal tract of animals when administered orally, or for reducing the populations of these bacteria which may be present as contaminants on the surfaces of the animal when applied externally. The process may be used for the treatment of a wide variety of animals, including humans. However, without being limited thereto, the process is preferably used for the treatment of meat-producing, ruminant and non-ruminant animals, such as bovine, fowl, porcine, ovine, and equine, and particularly cattle, chickens, turkeys, ducks, quail, geese, pigs, and sheep.

In a first preferred embodiment, the nitro compounds are administered orally to the subject animal for reducing (killing) populations of the enteropathogenic bacteria in the gastrointestinal tract. Typically, the compounds will be introduced into the alimentary tract by combining with the animal's feed or water, followed by oral ingestion thereof. However, it is also understood that the compounds may be administered separately or in combination with other conventional treatments. Although each of the nitro compounds are active against enteropathogenic bacteria over a broad range of conditions, the pH optima for activity are different. Notably, 2-nitroethanol and 2-nitropropanol exhibit optimal activity under slightly acidic conditions (i.e., pH between about 5 and 6) while 2-nitroethane exhibits optimal activity under slightly alkaline conditions (i.e., pH between about 8 and 9). It is therefore envisioned that the selection of the specific nitro compound to achieve optimal control may be influenced by the diet of the subject animal. For instance, animals fed on high grain diets, such as that fed to cattle on a feedlot or to broiler chickens, will typically have an acidic pH in the upper gastro-intestinal tract, particularly in the rumen or crop. For these animals, treatment with 2-nitroethanol and 2-nitropropanol would be preferred. Conversely, animals feeding on high roughage diets, such as grazing animals, will typically have an alkaline pH in the upper gastro-intestinal tract. For these animals, treatment with 2-nitroethane would be preferred.

In an alternative preferred embodiment, the nitro compounds are applied aerobically onto the outer surfaces of meat producing animals for reducing populations of the enteropathogenic bacteria on its head, torso and/or appendages. It is generally recognized that the hides, feathers, hair, feet and/or hoofs of such animals often become contaminated with fecal material, and may subsequently serve as sources for contamination with enteropathogenic bacteria. During slaughter, the carcasses or meat of the animals may become contaminated when contacted with any of these parts of the animal. In this embodiment, the compounds are preferably applied as a spray on the animal, although they may also be applied using other techniques such as dipping, or dusting. For these external applications, 2-nitropropanol and 2-nitroethanol are preferably formulated in a mild acid carrier at a pH between about 5 and 6, while nitroethane is preferably formulated in a mild alkaline carrier at a pH between about 8 and 9.

Treatment with the nitro compounds may occur at any time during the life of the animal. Moreover, significant reductions in the populations of enteropathogenic bacteria have been observed following treatment of an animal with as little as a single dose of one of the nitro compounds. As a practical matter however, greater control, that is, a further reduction in the populations of the enteropathogenic bacteria or in the incidence of infection thereby or the alleviation of symptoms of infection, may be effected by extending the treatment period. The actual duration of treatment may vary with the desired level of control, the subject animal and its physiological condition, and the dosage level, and may be readily determined by the practitioner skilled in the art. In one preferred embodiment, meat-producing animals are treated shortly before they are to be slaughtered, thereby reducing or eliminating the number of enteropathogenic bacteria present in the gut of each treated animal and reducing the incidence of contamination of the carcass or meat during slaughterhouse processing. Typically, the compounds will be orally administered to the animals just prior to shipment to slaughter facilities, or immediately upon arrival at such facilities. This will most often be within about 96 hours, particularly within about 48 hours, prior to slaughter. External application of the animals with the compounds will preferably occur within the same time period. In an alternative embodiment, animals may be treated with the compounds over extended periods of time, including long term, chronic treatments extending beyond three months and up to a year or more.

The nitro compounds are administered in an amount effective to control the population(s) of the target enteropathogenic bacteria in animals. An effective amount is defined herein as that amount which will significantly reduce or eliminate the population(s) of the target enteropathogenic bacteria, and/or reduce the incidence of infection by these bacteria, in a treated animal in comparison to untreated control animal. A reduction of incidence of infection may be demonstrated by a significant reduction in the number of animals infected or the severity or pathogenicity of infection, in comparison with untreated control animal. It is also understood that a reduction of incidence of infection may be demonstrated by a significant inhibition of intestinal, ruminal, or cecal colonization by the microorganism (as indicated by one or more of reducing pathogen shedding, reducing the average pathogen concentration, or lowering the percentage of animals colonized) in comparison with untreated controls. Suitable amounts may be readily determined by the practitioner skilled in the art, and will vary with the specific subject animal, its age, size, and physiological condition, and with the duration of treatment. Without being limited thereto, for administration of the compounds over relatively short term periods lasting for periods from 1 to 2 days up to approximately 3 months or less, suitable doses of the nitro compounds are typically greater or equal to than about 5 mg/day/kg and less than about 1 g/day/kg of body weight of the treated animal. It is anticipated that the preferred dosage ranges for such short term treatments of various meat producing animals are greater than or equal to about 5 mg/day/kg and less than about 900 mg/day/kg of body weight for poultry and swine, greater than or equal to about 20 mg/day/kg and less than about 300 mg/day/kg of body weight for cattle, and greater than or equal to about 5 mg/day/kg and less than about 100 mg/day/kg of body weight for sheep and goats. In contrast, for long term chronic treatments of the nitro compounds for periods extending beyond three months and lasting for a year or more, these doses may be significantly reduced, preferably reduced by up to as much as 100 fold for longer periods of administration.

Although pure or substantially pure nitro compounds may be administered to the animals directly, in an optional yet preferred embodiment they are provided in the animal's feed or water. Alternatively, the compounds may be further formulated with a conventional inert carrier or pharmaceutically acceptable carrier to facilitate administration. For example, without being limited thereto, all or a portion of the compounds may be encapsulated using techniques conventional in the art, including but not limited to encapsulation in alginate gels. When treating ruminant animals, a portion of the compounds is preferably encapsulated to allow higher concentrations of compounds to reach the hindgut of the animal, while still allowing for control of pathogenic bacteria in the rumen. The compounds may also be formulated with lactose or skim milk, or combined with a small amount of feed or water for use as a premix. Adjuvants conventional in the art for the treatment of the animals, including those for the treatment of enteropathogens, may also be formulated with the compounds. Suitable adjuvants include but are not limited to vaccines, antitoxins, deworming agents, or therapeutic antibiotics. Non-therapeutic levels of antibiotics may also be administered to the animals as is conventional in the art.

The following examples are intended only to further illustrate the invention and are not intended to limit the scope of the invention which is defined by the claims.

EXAMPLE 1

The bactericidal effect of 2-nitropropanol and nitroethanol were examined in vitro on several pathogenic bacteria including *Salmonella Typhimurium, Escherichia coli* O157:H7, *Campylobacter jejuni,* and *Enterococcus faecalis.* For an initial in vitro study 2-nitropropanol or nitroethanol were added to tryptic soy broth (TSB) medium in amounts to give 0, 2.5, 5, and 10 mM final concentration. Cultures were inoculated in TSB and incubated at 37° C. Specific growth rates ($h^{-1}$) were calculated by measuring optical density ($A_{600}$) with spectrophotometer. We observed that the growth of *S. Typhimurium* and *E. coli* O157:H7 was largely prohibited at 2.5 mM and higher concentrations of 2-nitropropanol or nitroethanol in TSB (FIG. 1). We also observed that growth of *E. faecalis* was markedly inhibited by 10 mM 2-nitropropanol 10 (FIG. 1) but was not tested against nitroethanol.

Figure 2:
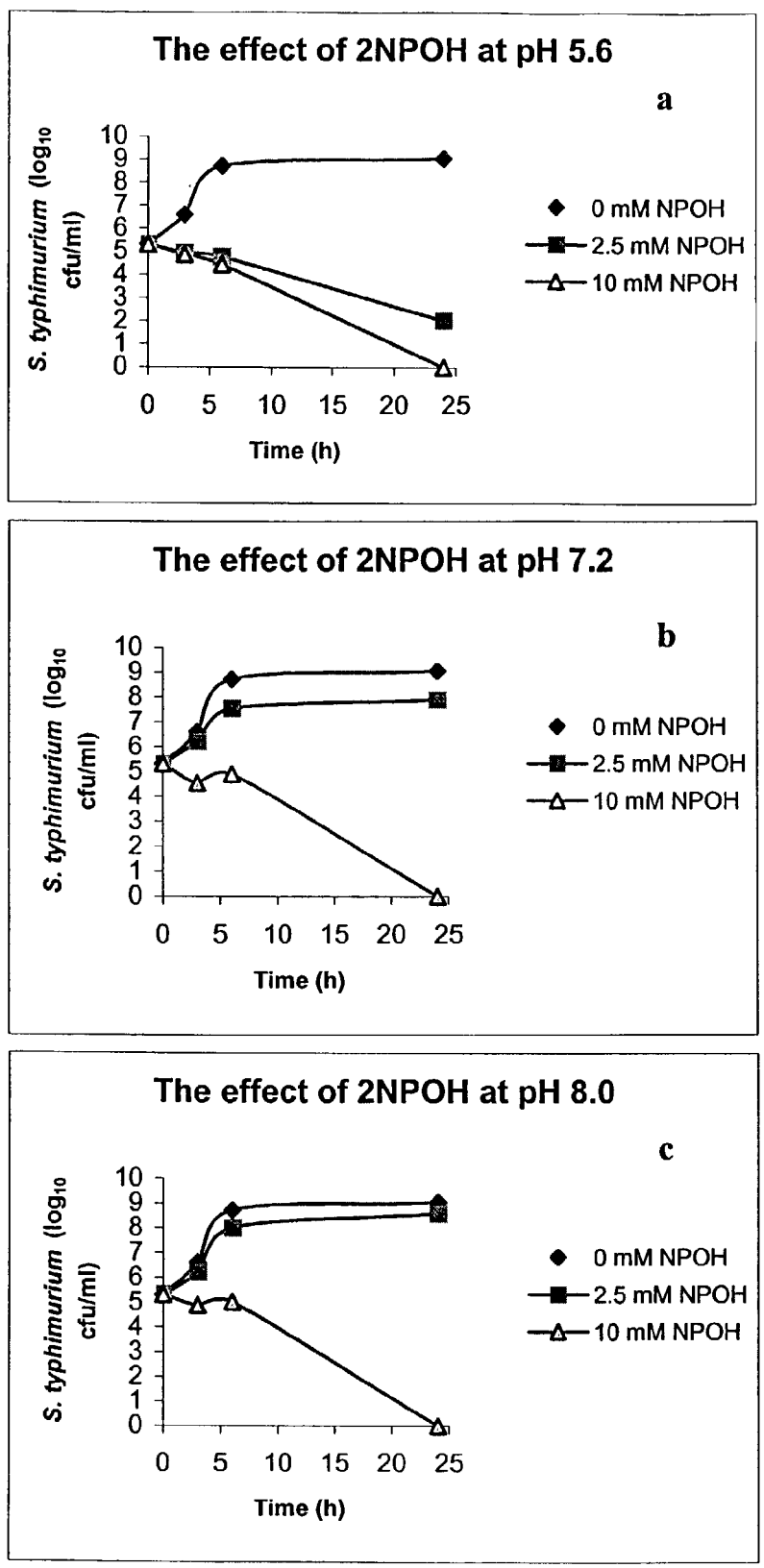
FIG. 2 shows the effect of 2-nitropropanol (2NPOH) on *S. typhimurium* in tryptic soy broth adjusted to pH at (a) 5.6, (b) 7.0, and (c) 8.2. Data points are mean values (n=2).

In order to observe the pH effect on this 2-nitropropanol, *S. Typhimurium* was inoculated into TSB medium adjusted to different pH (5.6, 7.2, and 8.0) with 2-nitropropanol (0, 2.5, and 10 mM final concentration) and incubated at 37° C. Populations of *S. Typhimurium* were determined (CFU/ml) by enumerating on tryptic soy agar (TSA) at 3, 6, and 24 h. After 24 h, cells were reduced approximately 3 log at 2.5 mM 2-nitropropanol at pH 5.6 but not in other pH ranges (7.2 and 8.0). However, *S. Typhimurium* was totally inactivated (more than 5 log reductions) at 10 mM 2-nitropropanol regardless of pH (FIG. 2).

Figure 3:
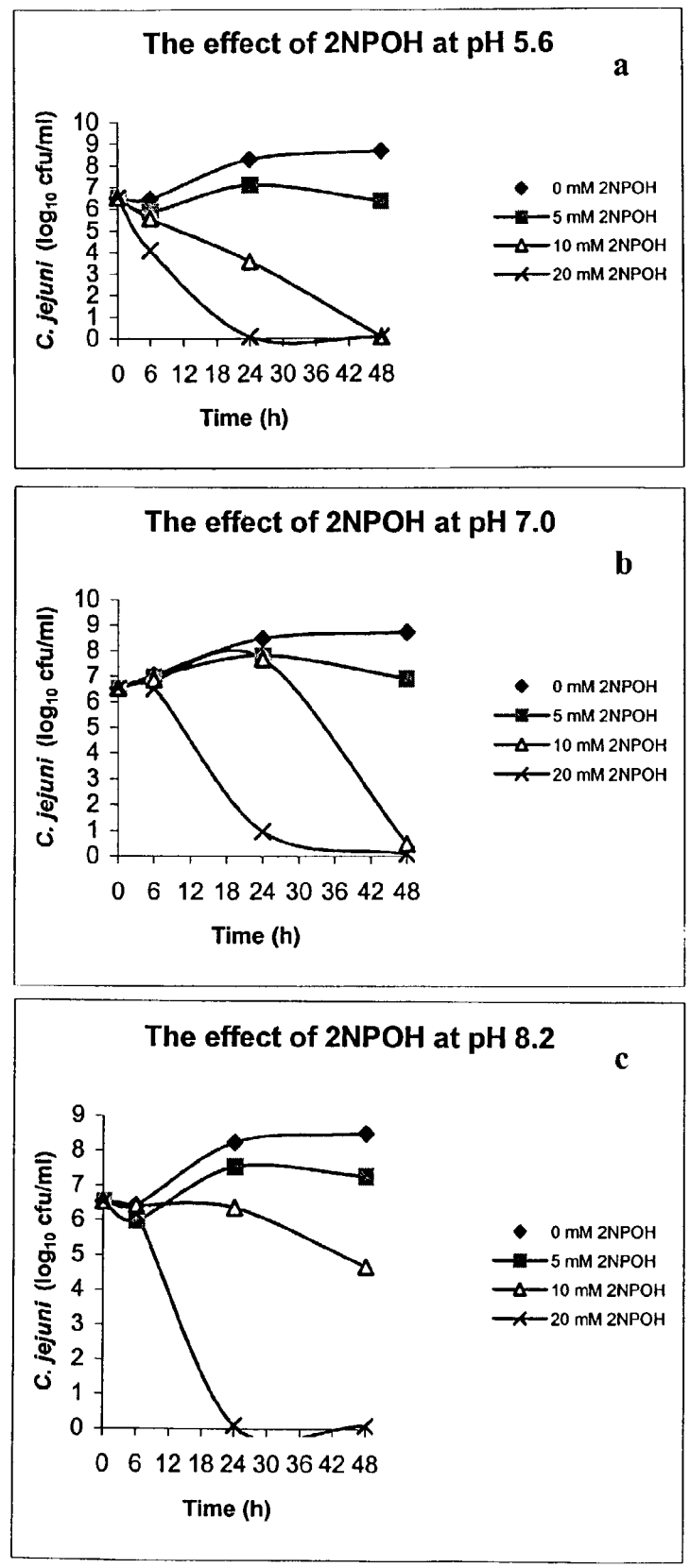
FIG. 3 shows the effect of 2-nitropropanol (2NPOH) on *Campylobacter jejuni* in *campylobacter* enrichment broth adjusted to pH at (a) 5.6, (b) 7.0, and (c) 8.2. Data points are mean values (n=2).

The bactericidal effect against *C. jejuni* was also determined in vitro. Cultures were inoculated into *Campylobacter* enrichment broth containing 2-nitropropanol at 0, 5, 10, and 20 mM of final and incubated at 42° C. We observed that *C. jejuni* cultures were completely inactivated at 10 mM and 20 mM concentration on 48 h at pH 5.6 and 7.0 verified by direct plating onto *Campylobacter*-cefex agar as well as qualitative enrichment procedure, while control (containing no 2-nitropropanol) showed cultures were reached to log 8 CFU/ml (FIG. 3). Taken together, both *Salmonella* and *Campylobacter* data indicate that the bactericidal effect is enhanced at acidic environment.

Figure 4:
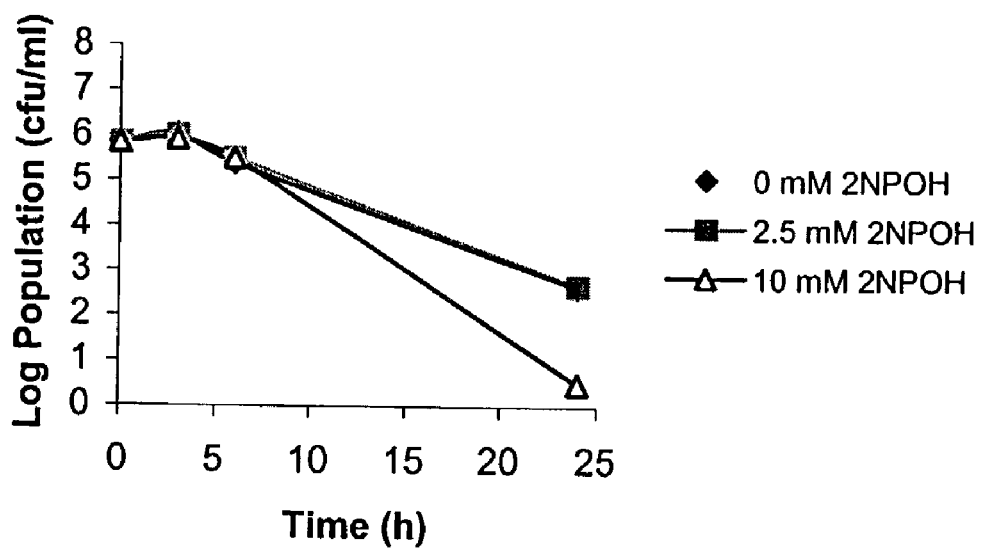
FIG. 4 shows the effect of 2-nitropropanol (2NPOH) with *Salmonella typhimurium* in (a) rumen and (b) fecal fluid. Data points are mean value (n=2).
Figure 4:
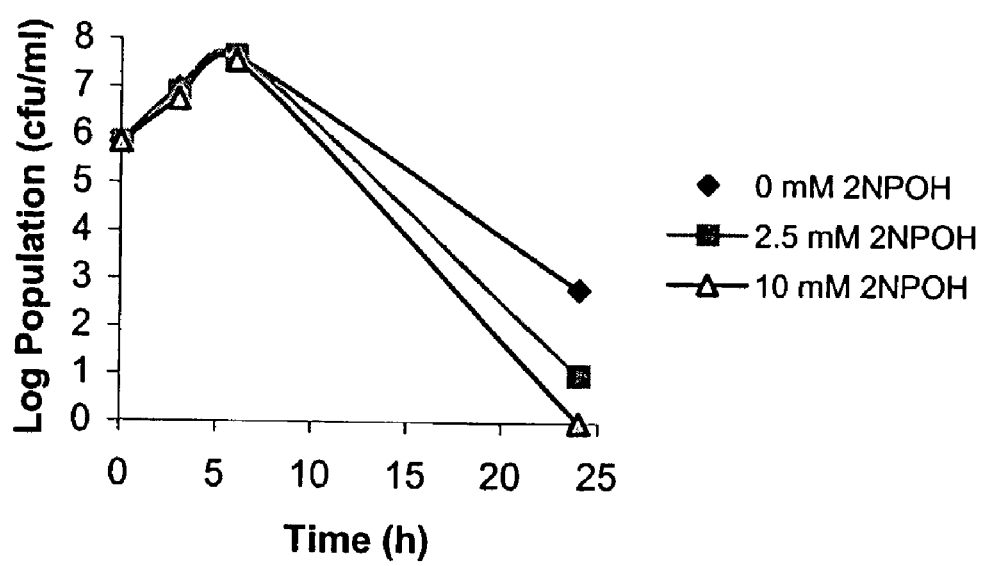

Another experiment was conducted to evaluate the bactericidal effect of 2-nitropropanol against *S. Typhimurium* in buffered rumen and fecal fluid containing viable populations of endogenous anaerobes. Briefly, ruminal contents and feces were retrieved and strained. Both collected fluids were transferred to laboratory and mixed with anoxic phosphate buffer (pH 6.8). Antibiotic-marked (25 µg novobiocin/ml and 20 µg/ml of nalidixic acid resistant) (NN)*S. Typhimurium* cultures were inoculated into these mixtures supplemented with 2-nitropropanol at various concentrations (0, 2.5, and 10 mM of final). Those inoculated tubes were incubated at 37° C. and populations were monitored at different sampling time (0, 3, 6, and 24 h) by direct plating onto brilliant green agar (BGA) containing NN. More than 2–3 log reductions of *Salmonella* populations were observed in both ruminal and fecal fluid containing 2-nitropropanol at 10 mM concentration compared to controls containing no 2-nitropropanol (FIG. 4).

EXAMPLE 2

The bactericidal effect of 2-nitroethane against *Campylobacter jejuni* was examined in vitro following substantially the same assay as described in the first experiment of Example 1 except Bolton Broth was utilized rather than TSB. In this experiment nitroethane was added to the Bolton Broth medium in amounts to give 0, 10, and 20 mM final concentrations, and trials were conducted in the media at different pH (5.6, 7.2, and 8.2).

Because 2-nitroethane is somewhat volatile, the sodium salt of the compound was prepared and used in this experiment. The salt was prepared using the process described by Majak et al. (1986, J. Anim. Sci., 62:1072–1080, the contents of which are incorporated by reference herein).

Figure 5:
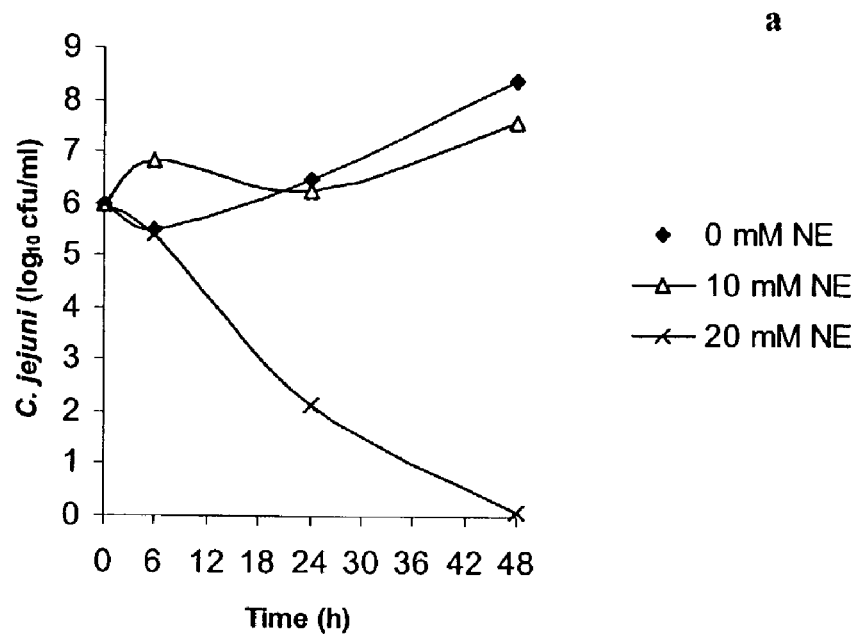
FIG. 5 shows the effect of nitroethane at different concentrations on *Campylobacter jejuni* in Bolton Broth adjusted to pH at (a) 5.6, (b) 7.0, and (c) 8.2. Data points are mean values (n=2).
Figure 5:
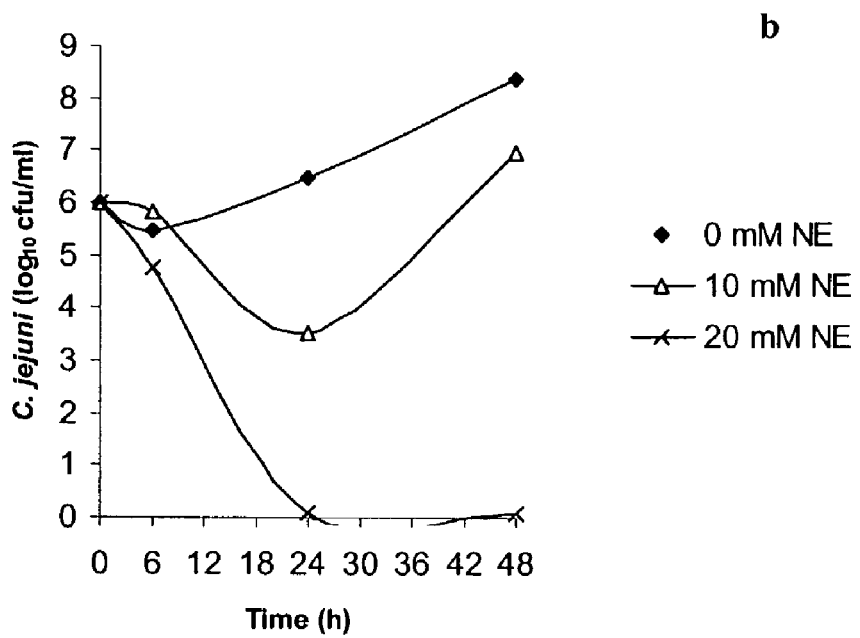
Figure 5:
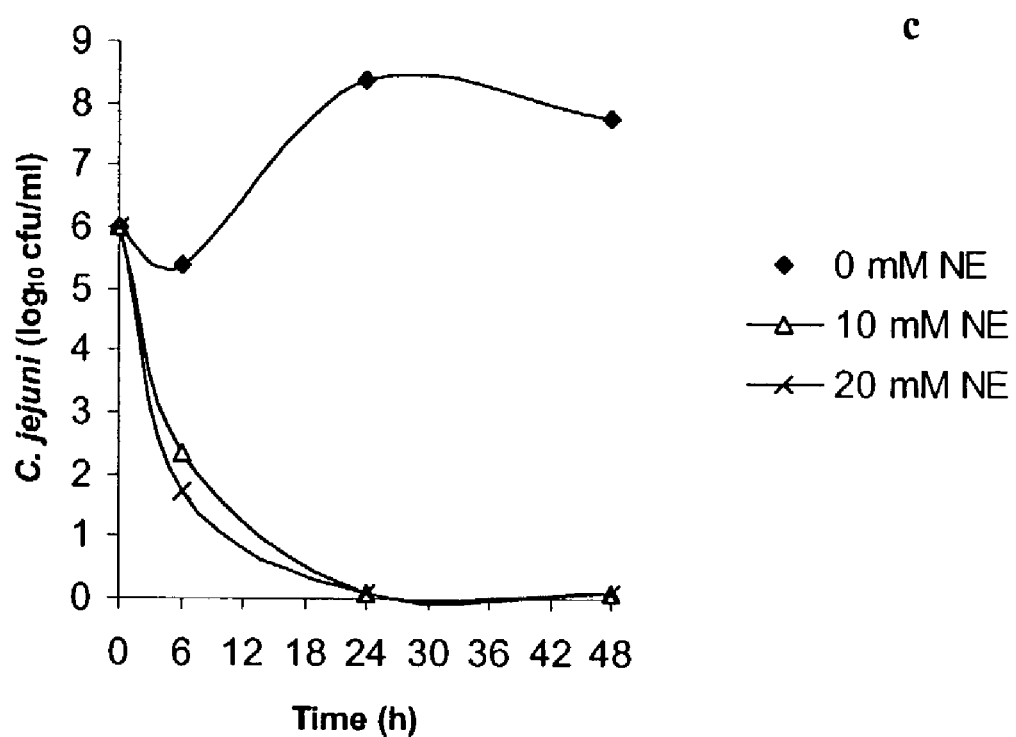

The results are shown in FIG. 5. Interestingly, in contrast to the findings with nitropropanol, the bactericidal effect of nitroethane increased at alkaline pH.

EXAMPLE 3

The bactericidal effect of 2-nitropropanol on *Salmonella typhimurium* was determined in vivo. The in vivo study was conducted using 7-day-old chick experimentally infected with *S. Typhimurium*. In experiment 1, chicks were orally challenged with $10^6$ cfu of NN-resistant strain of *S. Typhimurium*. Chicks were divided into four groups; control, 1 (13 mg 2-nitropropanol/bird), 5 (65 mg 2-nitropropanol/bird) and 10×(130 mg 2-nitropropanol/bird). Treatments were administered via oral gavage. After 24 h, cecal contents were aseptically removed and subjected to bacterial analysis. Mean±SD populations ($Log_{10}$ CFU/g) of *S. Typhimurium* were reduced (P<0.05) in all groups receiving 2-nitropropanol (1×, 5×, and 10×) comparing to untreated controls (3.65±2.01, 3.39±2.42, 3.47+1.55 versus 6.09±1.02, respectively) (Table 1).

Table 2 shows results from experiment 2. Significant (P<0.05) log reductions occurred in group administered 1×(13 mg/bird) dose for both 24 and 48 h duration compared to untreated control. Regardless of time effect, combined data also indicates that the populations recovered from 1×dose treated group were significantly different (P<0.05) comparing to control (2.73±2.45 versus 4.83±2.11).

EXAMPLE 4

The bactericidal effect of 2-nitropropanol against *Listeria monocytogenes* was examined in vitro following the same assay as described in the first and second experiments of Example 1. Trials were conducted in the media at different pH (5.6, 7.2, and 8.2).

Figure 6:
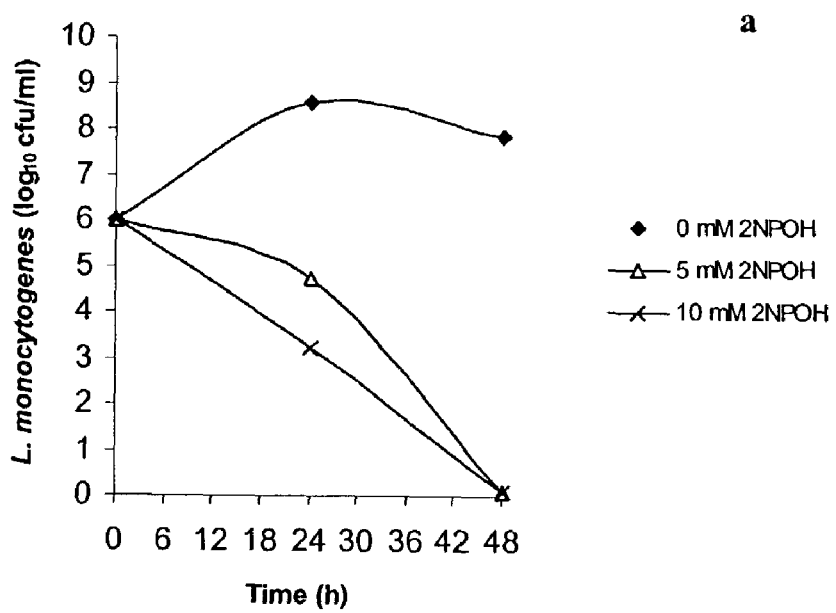
FIG. 6 shows the effect of 2-nitropropanol at different concentrations on *Listeria monocytogenes* in Tryptic Soy Broth adjusted to pH at (a) 5.6, (b) 7.0, and (c) 8.2, all at 37° C. Data points are mean values (n=2).
Figure 6:
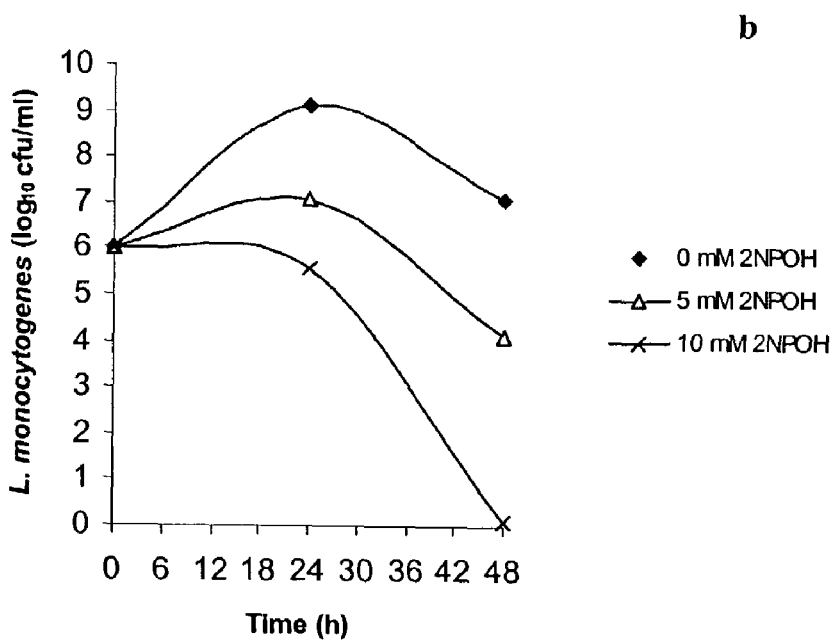
Figure 6:
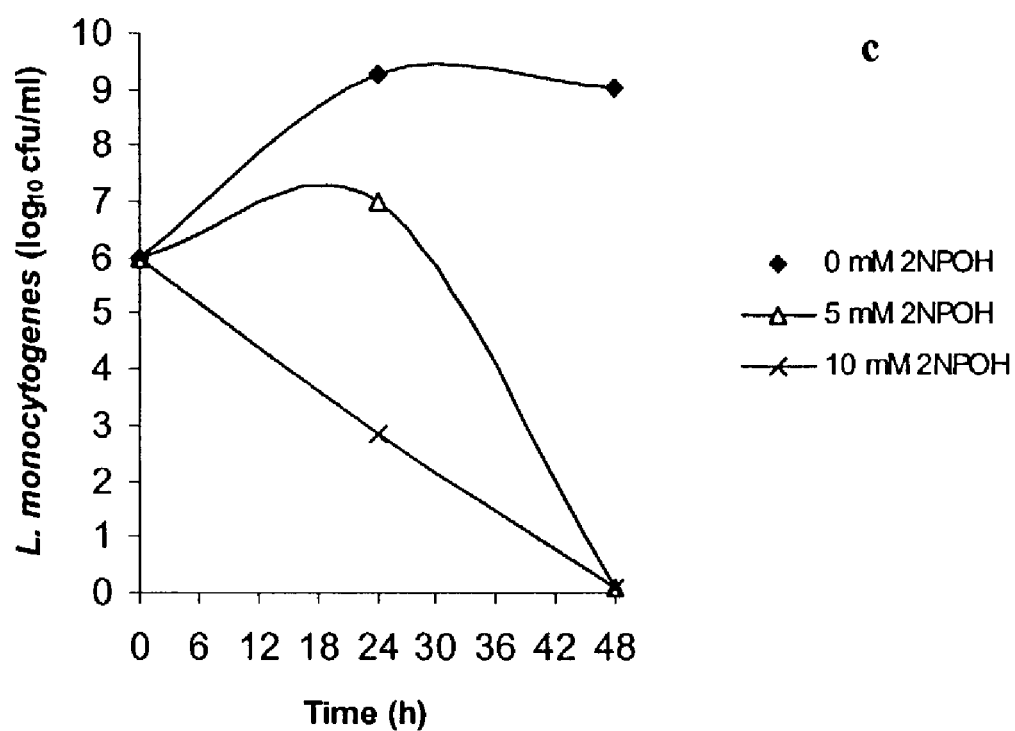

The results are shown in FIG. 6. The data indicate that the bactericidal effect is enhanced in an acidic or alkaline environment, but is somewhat reduced at neutral pH.

It is understood that the foregoing detailed description is given merely by way of illustration and that modifications and variations may be made therein without departing from the spirit and scope of the invention.

TABLE 1

Effect of 2-nitropropanol treatment on cecal *Salmonella Typhimurium* populations following experimental challenge in 1-wk-old broiler chicks.

| Treatment[b] | n[c] | Experiment 1[a] Mean log CFU/g of cecal content[d] (standard deviation) |
|---|---|---|
| Control | 10 | 6.09 (1.03) A |
| 1× | 10 | 3.65 (2.01) B |
| 5× | 9 | 3.39 (2.42) B |
| 10× | 7 | 3.46 (1.55) B |

[a]Broilers were challenged with ca. log 6 per bird of nalidixic acid and novobiocin resistant *S. Typhimurium* strain on 6 day prior to slaughter.
[b]2-Nitropropanol was administered via oral gavage at 0 (control), 13 (1×), 65 (5×), and 130 mg (10×) per bird for 24 h duration. Control birds were not treated with 2-nitropropanol.
[c]Number of cecal samples analyzed on this trial.
[d]Means within columns with different letters are significantly different (P < 0.05).

TABLE 2

Effect of 2-nitropropanol treatment on cecal *Salmonella Typhimurium* populations following experimental challenge in 1-wk-old broiler chicks.

| Treatment[b] | *Salmonella Typhimurium*, Mean log CFU/g of cecal content[a] (standard deviation) | | |
|---|---|---|---|
| | 24 h | 48 h | Combined |
| Control | 4.64 (1.79) A | 5.03 (2.42) A | 4.83 (2.11) A |
| 0.5× | 4.19 (2.53) A | 3.84 (2.69) AB | 4.01 (2.59) A |
| 1× | 2.58 (2.10) B | 2.88 (2.78) B | 2.73 (2.45) B |

[a]Broilers were challenged with ca. log 6 per bird of nalidixic acid and novobiocin resistant *S. Typhimurium* strain on 3 day prior to slaughter. Means within columns with different letters are significantly different (P < 0.05); n = 20 for all treatment group at 24 h and 48 h except 0.5× (n = 19) in 24 h.
[b]2-Nitropropanol was administered via oral gavage at 0 (control), 6.5 (0.5×), and 13 mg (1×) per bird for 24 and 48 h duration. Control birds were not treated.

We claim:

1. A method for controlling bacterial enteropathogenic *Salmonella* species, enteric *Escherichia coli* pathogens, *Campylobacter* species, or *Listeria monocytogenes*, in a non-ruminant animal comprising orally administering to said non-ruminant animal a nitro compound selected from the group consisting of 2-nitropropanol, 2-nitroethane, 2-nitroethanol, salts thereof, and mixtures thereof, in an amount effective to inhibit growth of said bacterial enteropathogenic *Salmonella* species, enteric *Escherichia coli* pathogens, *Campylobacter* species, or *Listeria monocytogenes*.

2. The method of claim 1 wherein said compound is selected from the group consisting of 2-nitropropanol, 2-nitroethane, and 2-nitroethanol.

3. The method of claim 1 wherein said nitro compound is formulated in a composition with a carrier.

4. The method of claim 3 wherein said carrier comprises a pharmaceutically acceptable carrier.

5. The method of claim 1 wherein said administering comprises providing said nitro compound in combination with water for said animal.

6. The method of claim 1 wherein said administering comprises providing said nitro compound in combination with feed for said animal.

7. The method of claim 1 wherein said nitro compound is encapsulated.

8. The method of claim 1 wherein said amount is between about 5 mg/day/kg to about 1 g/day/kg of body weight of said animal.

9. The method of claim 1 wherein said animal is selected from the group consisting of fowl, equine, and porcine.

10. The method of claim 9 wherein said animal is a fowl.

11. The method of claim 9 wherein said animal is selected from the group consisting of fowl and porcine and said amount is between about 5 mg/day/kg to about 900 mg/day/kg of body weight of said animal.

12. The method of claim 1 wherein said animals are treated with said nitro compound within about 48 hour prior to slaughter thereof.

13. A method for controlling bacterial enteropathogenic *Salmonella* species, enteric *Escherichia coli* pathogens, *Campylobacter* species, or *Listeria monocytogenes*, on the surface of an animal comprising externally applying a composition of a nitro compound selected from the group consisting of 2-nitropropanol, 2-nitroethane, 2-nitroethanol, salts thereof, and mixtures thereof, onto said animal in an amount effective to inhibit growth of said bacterial enteropathogenic *Salmonella* species, enteric *Escherichia coli* pathogens, *Campylobacter* species, or *Listeria monocytogenes*.

14. The method of claim 13 wherein said composition of said nitro compound is applied onto the head, torso or appendages of said animal.

15. The method of claim 13 wherein said applying is selected from the group consisting of spraying, dipping, and dusting.

16. The method of claim 13 wherein said composition comprises said nitro compound with a liquid carrier.

17. The method of claim 16 wherein said composition comprises an aqueous composition of said nitro compound.

18. The method of claim 13 wherein said compound is selected from the group consisting of 2-nitropropanol, 2-nitroethane, and 2-nitroethanol.

19. The method of claim 13 wherein said nitro compound is a salt and said composition comprises said salt with a solid carrier.

20. The method of claim 13 wherein said animal is selected from the group consisting of fowl, bovine, equine, and porcine.

21. The method of claim 1 wherein said compound is selected from the group consisting of 2-nitropropanol, salts thereof, and mixtures thereof.

22. The method of claim 1 wherein said compound is selected from the group consisting of 2-nitroethane, salts thereof, and mixtures thereof.

23. The method of claim 1 wherein said compound is selected from the group consisting of 2-nitroethanol, salts thereof, and mixtures thereof.

* * * * *